United States Patent [19]

Masson

[11] Patent Number: 4,580,452
[45] Date of Patent: Apr. 8, 1986

[54] DEVICE FOR TAKING A LIQUID FROM A CONDUIT WHICH CONTAINS THE LIQUID OR FOR INJECTING A LIQUID INTO THE CONDUIT

[76] Inventor: Guy Masson, 1931 Sarreyer, Canton of Valais, Switzerland

[21] Appl. No.: 648,325

[22] Filed: Sep. 7, 1984

[30] Foreign Application Priority Data

Sep. 13, 1983 [CH] Switzerland ............... 976/83

[51] Int. Cl.[4] ............................................. G01N 1/00
[52] U.S. Cl. .................................................. 73/863.86
[58] Field of Search ............... 73/863.86, 863.11, 40.7, 73/46; 137/240; 251/335

[56] References Cited

U.S. PATENT DOCUMENTS

| | | | |
|---|---|---|---|
| 2,041,694 | 5/1936 | Buckley | 73/863.11 |
| 2,691,773 | 10/1954 | Lichtenberger | 73/46 |
| 3,278,156 | 10/1966 | Callahan | 251/335 |
| 3,744,319 | 7/1973 | Harmes | 137/240 |
| 4,150,575 | 4/1979 | Magorien | 73/863.86 |
| 4,320,654 | 3/1982 | Collins | 73/40.7 |
| 4,458,543 | 7/1984 | Mieth | 73/863.86 |

FOREIGN PATENT DOCUMENTS

| | | | |
|---|---|---|---|
| 363890 | 12/1972 | U.S.S.R. | 73/863.86 |
| 549706 | 3/1977 | U.S.S.R. | 73/863.86 |

*Primary Examiner*—Stewart J. Levy
*Assistant Examiner*—Robert R. Raevis
*Attorney, Agent, or Firm*—Silverman, Cass & Singer, Ltd.

[57] ABSTRACT

A valve is mounted on a conduit from which it is desired to take a sample of the liquid which flows along the conduit. The body of the valve includes a through passage within which a needle valve member is removably inserted to close the valve. The body is provided, opposite said passage, with a collar in which is engaged the end of a rigid tube with a sampling vessel provided with a needle valve. Thus, it is possible to withdraw samples of the liquid into the vessel without any leakage of liquid and even without any emanation therefrom occuring, which is of the highest importance in the case of toxic or noxious liquids. Moreover, the device does not produce any dead volume of liquid which it would be necessary to purge before each taking or sampling of liquid from the conduit.

10 Claims, 5 Drawing Figures

DEVICE FOR TAKING A LIQUID FROM A CONDUIT WHICH CONTAINS THE LIQUID OR FOR INJECTING A LIQUID INTO THE CONDUIT

BACKGROUND OF THE INVENTION (a) Field of the Invention

The present invention relates to a device adapted to allow taking of a liquid from a conduit which contains the liquid, or the injection of a liquid into said conduit.

The device of the invention will be used mainly in the field of chemistry or in the nuclear industry where, especially during manufacturing processes, it is useful to take samples of liquids, which are often injurious, with which not only the operator must not enter into contact, but of which the emanations therefrom can themselves be dangerous.

(b) Description of the Prior Art

Up to the present, such sampling has been effected merely by means of cocks mounted on the conduct in which the liquid to be taken is flowing, while taking care to prevent any leakage and maintaining at a minimum the emanations from the liquid. In more sophisticated installations, the sampling cock has been surrounded with a protective aspiration box to aspirate the gas issuing from the taken liquid. Such installations are complicated, inconvenient to use and, moreover, discharge into the atmosphere the noxious emanations.

Moreover, with the conventional sampling devices, there generally remains a dead volume of liquid which, after each sample has been taken, has to be purged before the next sampling, while taking the same precautions with respect to the noxious character of the liquid as for the sampling itself.

The conduits, in order to enable sampling, have also been provided with passages closed by membranes (septum) which are for the taking of a sample pierced by the needle of a syringe, of the type referred to as hypodermic syringes. This system is, however, not satisfactory since the membrane becomes hard, in use, and there is a risk of it rupturing under the effect of the pressure exerted thereon by the liquid in the conduit; furthermore, it does not satisfactorily resist the action of corrosive liquids.

SUMMARY OF THE INVENTION

The object of the present invention is to overcome the foregoing drawbacks of prior sampling arrangements.

This object is achieved due to the fact that a device according to the invention comprises a valve mounted on the conduit, the body of the valve being pierced with a through flow passage and containing a needle valve member for closure of said passage, and the valve member being operable from the outside of the valve.

The various features of the invention will be apparent from the following description, drawings and claims, the scope of the invention not being limited to the drawings themselves as the drawings are only for the purpose of illustrating embodiments in which the principles of the invention can be applied. Other embodiments of the invention utilizing the same or equivalent principles may be used and structural changes may be made as desired by those skilled in the art without departing from the present invention and the purview of the appended claims.

DESCRIPTION OF THE PREFERRED EMBODIMENTS

Figure 1:
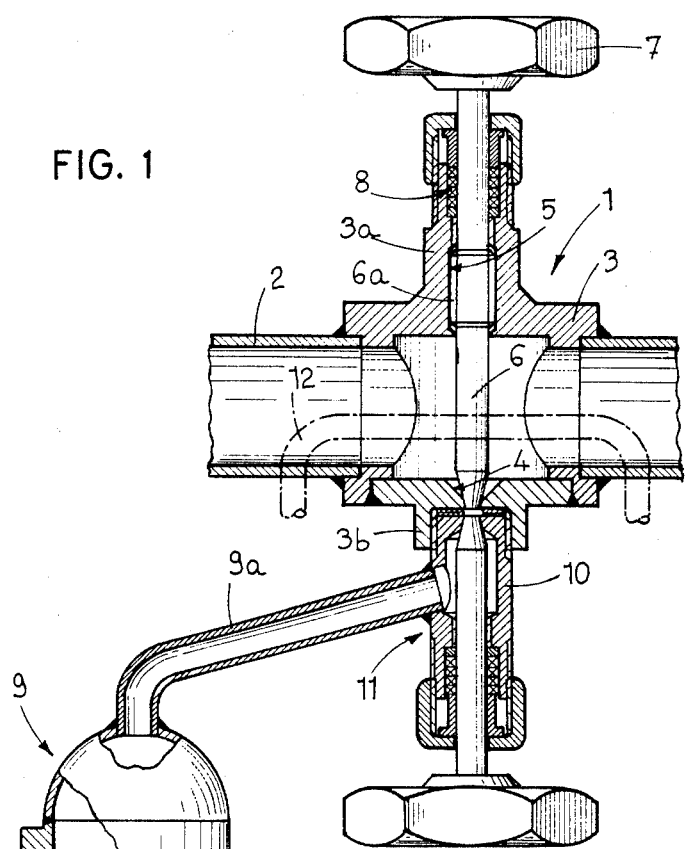
FIG. 1 is a sectional view of a first embodiment of a device enabling a sample of a toxic liquid to be taken.

The sample taking device illustrated in FIG. 1 comprises a valve, generally designated by reference 1, which is mounted on a conduit 2 forming part of a chemical plant installation. The body 3 of this valve, which is cylindrical, is pierced at its lower part with a through passage 4.

The body 3 is provided, diametrically opposite to the passage 4, with a collar 3a, which is internally threaded at 5 and traversed by a threaded portion 6a of a stem 6 of a needle valve member closing the passage 4. A controlling hand-wheel 7 is mounted on the rear outer end of the stem of the needle member and thus enables axial displacement of this needle member and, consequently, the opening and closing of the passage 4 to be produced by rotation of the handwheel in one sense or the other. A stuffing box 8 ensures a tight seal around the stem 6 of the needle member.

The sample taking device comprises moreover a vessel, generally designated by reference 9, which is prolongated by a tubular portion 9a, the end of which is secured to the body 10 of a needle valve generally designated by reference 11. The body 10 is intended to engage a collar 3b of the body 3 of the valve 1 situated opposite to the passage 4, that is to say diametrically opposed to the collar 3a.

As a modification, the valve 1 can be traversed by a conduit, such as the conduit 12 indicated in dash-and-dot lines in FIG. 1, intended for the circulation of a heating fluid the purpose of which is to prevent crystallization of the sampled liquid, some products crystallizing at temperatures of approximately 20° C.

When the liquid flowing through the conduit 2 is sampled, the end of the body 10 of the valve 11 of the vessel 9 is inserted into the collar 3b and the valve 11 then opened. The needle member 6 is then moved to a valve-open position and the sampled liquid flows into the vessel 9. The needle member 6 is closed, then the valve 11, so that the sampling is effected not only without a drop of liquid escaping, but also without any emanation therefrom occuring. Moreover, when the needle member 6 is closed anew, it does not isolate any dead volume of liquid which it would be necessary to purge at the time of the next sampling.

Figure 2:
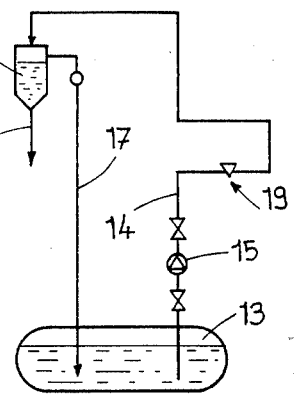
FIG. 2 shows, very diagrammatically, a chemical installation provided with the sample taking device of FIG. 1.

FIG. 2 shows a chemical installation in integrating the liquid sampling device of FIG. 1.

This installation comprises a vessel 13 containing a reaction product such as a liquid containing phosgene or dichlorethane intended to be conveyed, through a conduit 14 and by means of a pump 15, into a feed-tank 16. A waste-pipe 17 conducts the excess of product back into the tank 13, while a conduit 18, in communication with the bottom of the feed-tank 16, conveys the product towards the chemical equipment where it is to be used. The liquid taking or sampling device, diagrammatically indicated at 19 in FIG. 2, and which corresponds to the device of FIG. 1, is mounted on the conduit 14 and enables sampling of the product without any risk the operator comes into contact therewith or even that noxious emanations therefrom might occur.

Figure 3:
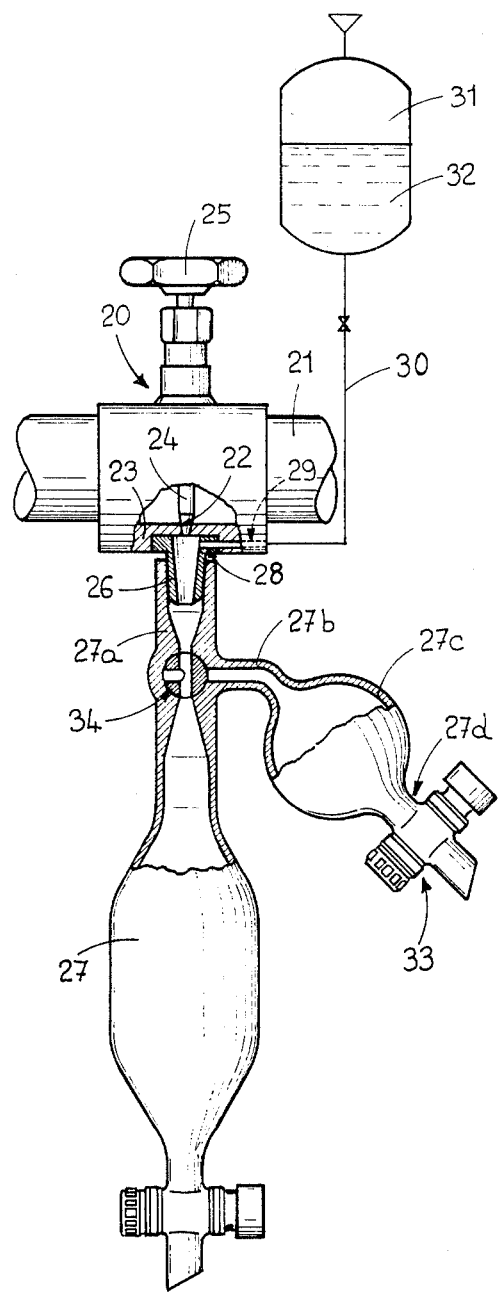
FIG. 3 is an elevational view, with partial section, of a second embodiment of a sample taking device in accordance with the invention.

The liquid sample taking device illustrated in FIG. 3 comprises a valve 20, similar to the valve 1 of the first embodiment, which is mounted on a conduit 21. The sampling passage, designated by reference 22, provided in the body 23 of the valve, is closed by a needle valve member 24 operable by a control handwheel 25. The body 23 of the valve carries, situated opposite the passage 22, an adaptor 26 intended to engage the collar, designated by reference 27a, of a sample-receiving vessel 27. The body 23 and the adaptor 26 have through passages 29 and 28, respectively, connected by a conduit 30 to a tank 31 containing a cleaning liquid 32. This liquid can be directed through the conduit 30, after the taking of a sample, on to the opening of the sampling passage 22 for the purpose of cleaning the latter.

The collar 27a of the vessel 27 is provided with a lateral branch 27b prolongated by a bulb 27c constituting the receiving vessel for the cleaning liquid. This liquid is evacuated through the tubular branch 27b on which is mounted a manually operable valve 33. A three-way cock 34 which is also manually operable can be brought into two different and alternative positions; one, shown in the drawing, where the branch 27b is closed and the vessel 27 is open, which corresponds to the sampling position, and the other one where the branch is open and the vessel closed, which is the cleaning position.

Figure 4:
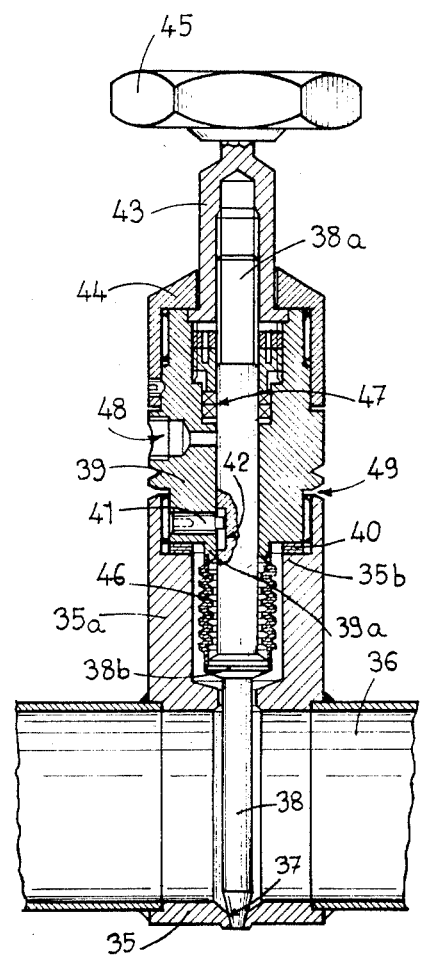
FIG. 4 is an axial sectional view of a third embodiment of a sample taking device, the single valve of which has been shown.

In the embodiment of FIG. 4, the illustrated valve comprises a cylindrical body 35 mounted on a conduit 36 containing the fluid of which it is desired to take samples. This body 35 has a through sampling passage 37 closed by a needle valve member 38.

The body 35 of the valve is provided, diametrically opposed to the passage 37, with a collar 35a in which is screwed a cap 39 which bears on an inner shoulder 35b of the collar 35a through the intermediary of a sealing gasket 40. The cap 39 carries a radial screw 41 engaged in a longitudinal groove 42 of the needle member 38 to prevent the latter rotating about its axis. A control member 43, having the shape of an internally screw-threaded sleeve, is rotatably mounted on the cap 39 on which it is held captive by a ring 44. This control member 43, which is rigid with a handwheel 45, is screwed on the end 38a of the needle member 38 which is threaded so that turning the handwheel 45 in one sense or the other produces corresponding axial displacement, in one directional sense or the other, of the needle member 38.

The sealing of the valve is ensured by an extensible sealing bellows 46, made of a material resistant to the action of the liquid to be sampled and which is secured on the one hand to an annular shoulder 38b of the needle member and, on the other hand, to a sleeve portion 39a at the inner end of the cap 39. For the case where leakages would occur at the level of the extensible sealing bellows 46, the valve is moreover provided with a stuffing box 47 ensuring a tight seal between the needle member 38 and the cap 39.

The cap is pierced with a tapped radial passage 48 in which can be fixed a conduit connected to a gas analyzer arranged in such a way as to detect any gas emanating from the liquid to be sampled and, consequently, to detect leakage of the sealing bellows 46.

As a modification, the sealing gasket 40 could be replaced by a continuous circumferential weld at 49, between the cap 39 and the collar 35a of the body 35 of the valve. In this case, the screw 41 should be situated higher, further along the cap 39, so as to be situated beyond the sealed joint constituted by the circumferential weld.

Figure 5:
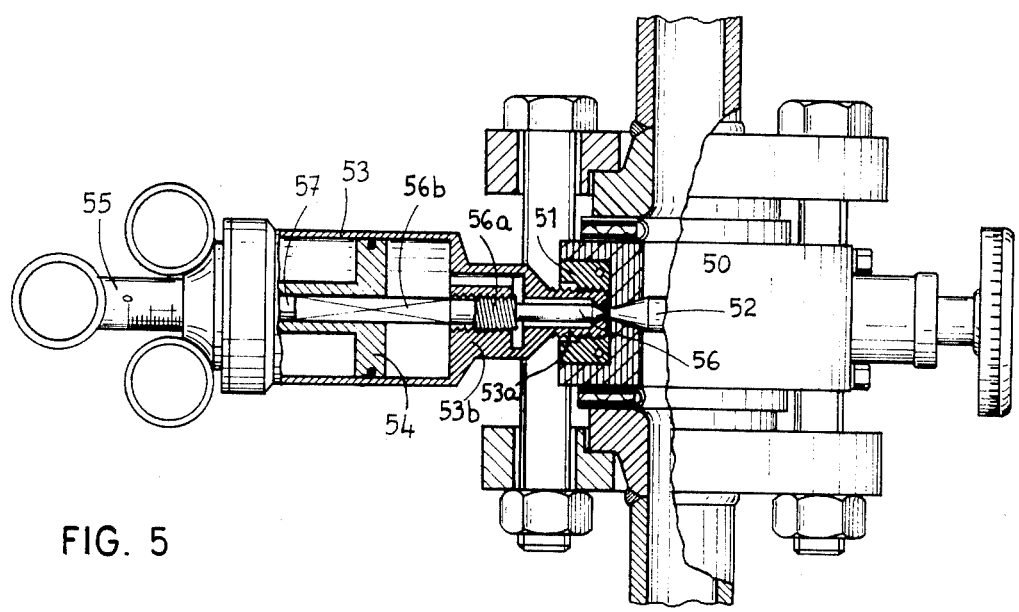
FIG. 5 is an elevational view, with partial section, of a fourth embodiment comprising means which enable a liquid to be injected into the conduit or to be taken therefrom.

In the embodiment of FIG. 5, the body of the valve, designated by reference 50, is provided with a tapped opening 51 which is situated in an extension of the passage closed by the needle valve member which is designated by reference 52. This tapped opening is intended to receive the threaded end, designated by reference 53a, of the body 53 of a syringe the piston of which, designated by reference 54, is operable by means of a stem 55. This syringe contains a needle valve member 56 provided with a screw-threaded portion 56a screwed into a tapped portion 53b of the body 53. This needle member terminates in a portion 56b of square crosssection and is engaged in a longitudinal passage 57, which is of corresponding cross-section, provided in the piston 54. Thus, rotating the stem 55 of the piston and, consequently, the piston itself, also rotates the needle member 56 which is deeply screwed in the portion 53b of the body of the syringe. The needle can thus be brought into a position in which it closes the end of the syringe and thus serves, after an injection of liquid as well as after a taking of liquid, to prevent any leakage of liquid, with the end of the needle member 56 of the syringe practically in contact with the end of the needle member 52 of the sampling or injecting valve.

It should be noted that the valve, whatever the actual embodiment may be, can be motorized, that is to say the opening and closing of the valve can be controlled by a motor instead of being produced manually.

I claim:

1. A device for taking a sample of a liquid flowing through a conduit or for injecting a liquid into the conduit, comprising:
   A. a valve body including a wall forming a portion of said conduit, said wall having a sample passage therethrough including an opening through an outer surface of said wall; and
   B. a needle member operable from outside the valve body and removably passing through said passage to form a needle valve therewith, said needle member having one end thereof passing through said passage and located in flush engagement with said outer surface of said wall in a closed position of said needle valve so that said member completely occupies said opening in order to eliminate any dead volume within said passage isolated from said flow through said conduit in said closed position, which dead volume would otherwise expose a portion of the wall surrounding said passage to adhesion of static sample liquid in said closed position and would otherwise require purging of said passage between liquid samplings.

2. A device as claimed in claim 1, in which a rear part of a stem of the needle member passes through the wall of said body of the valve, which is cylindrical, at a point situated diametrically opposite to the point at which said passage is situated, a seal between the body of the valve and said needle member being ensured by a stuffing box.

3. A device as claimed in claim 2, in which said body of the valve is provided, at a location where said wall is traversed by the needle member, with an internally tapped bore in which is screwed a threaded portion of said stem of the needle member, so that rotation of the needle member in one sense or the other produces corresponding axial displacement of the needle member.

4. A device as claimed in claim 1, in which the needle is rigid with an axially deformable bellows the end of which is secured, in a sealed manner, to said body of the valve.

5. A device as claimed in claim 4, in which said body of the valve carries, rotatably mounted thereon, a control member which is screwed on a screw-threaded rear portion of an operating stem of the needle member, so that rotation of this control member, in one sense or the other, produces corresponding axial displacement of said stem.

6. A device as claimed in claim 4, in which the valve is provided with means enabling connection to a portion situated beyond the sealing bellows, with respect to its portion traversed by the liquid to be taken from the conduit, to a gas analyzer intended to detect any emanation of gas from the liquid to be taken and, hence, any leakage of the sealing bellows.

7. A device as claimed in claim 1, in which said valve is traversed by a conduit adapted for circulation of a heating fluid to heat the liquid to be taken.

8. A device as claimed in claim 1, which comprises a sampling vessel provided with a collar an end of which is arranged in such a way as to be able to come in close contact with the area of the body of the valve in which is disposed said through passage.

9. A device as claimed in claim 7, in which said body of the valve includes a second conduit opening adjacent the opening of the through passage, for enabling a cleaning liquid to be fed to the opening of said through passage.

10. A device as claimed in claims 7 and 9, in which said collar of the sampling vessel is provided with a branch enabling the evacuation of said cleaning liquid, a valve serving to control the communication of the vessel with the outside being a three-way valve serving also to control the communication of said branch with the outside of the vessel, the arrangement being such that, according to the position of said three-way valve, either the vessel is open and the branch closed, or the vessel is closed and the branch open.

* * * * *